United States Patent [19]

Kondo et al.

[11] 4,390,475

[45] Jun. 28, 1983

[54] THIN FILM TYPE SULFONATION PROCESS OF ALKYLBENZENE

[75] Inventors: Fusao Kondo; Toshimi Terao, both of Chiba; Katsumasa Nagano, Ichikawa; Kyozo Kitano, Chiba, all of Japan

[73] Assignee: Lion Corporation, Tokyo, Japan

[21] Appl. No.: 306,504

[22] Filed: Sep. 28, 1981

Related U.S. Application Data

[63] Continuation-in-part of Ser. No. 163,162, Jun. 26, 1980.

[30] Foreign Application Priority Data

Jul. 6, 1979 [JP] Japan .................................. 54-86252

[51] Int. Cl.³ ........................................... C07C 143/24
[52] U.S. Cl. .............................. 260/505 S; 260/505 E
[58] Field of Search ......................... 260/505 E, 505 S

[56] References Cited

U.S. PATENT DOCUMENTS

| | | | |
|---|---|---|---|
| 2,723,990 | 11/1955 | Flushing et al. | 260/505 |
| 3,270,038 | 8/1966 | Timperley et al. | 260/400 |
| 3,328,460 | 6/1967 | Vander Mey | 260/505 |
| 4,113,765 | 9/1978 | Richardson et al. | 260/505 |

FOREIGN PATENT DOCUMENTS 53-63346 6/1978 Japan .

Primary Examiner—Alan Siegel
Attorney, Agent, or Firm—Armstrong, Nikaido, Marmelstein & Kubovcik

[57] ABSTRACT

Alkylbenzene is sulfonated in a thin film type sulfonation process by adding 2 through 20 parts by weight, based on 100 parts by weight of said alkylbenzene, of alkylbenzene sulfonic acids having alkyl groups of 1 through 20 carbon atoms and/or benzene sulfonic acids to the alkylbenzene prior to the contact thereof with diluted gaseous sulfur trioxide. The addition of alkylbenzene sulfonic acids and/or benzenesulfonic acid effectively prevents the formation of adherent deposits on the surface of a reaction wall.

6 Claims, No Drawings

THIN FILM TYPE SULFONATION PROCESS OF ALKYLBENZENE

CROSS-REFERENCE TO RELATED APPLICATIONS

This application is a continuation-in-part of patent application Ser. No. 163,162, filed June 26, 1980.

BACKGROUND OF THE INVENTION

1. Field of the Invention

This invention relates to an improvement in or relating to a thin film type sulfonation process of alkylbenzenes. More specifically, it relates to a process for preventing the deposition of partially carbonized adherent deposits onto the surface of a reaction wall in a thin film type sulfonation process of alkylbenzenes.

2. Description of the Prior Art

It has been heretofore known in the art, as one process for sulfonating alkylbenzenes, that, while a feed stream of starting alkylbenzenes is flowed downward in the form of a thin film along a surface of a reaction wall of a sulfonation reactor, the thin film stream of the alkylbenzenes is contacted with a gas stream of gaseous sulfur trioxide ($SO_3$) diluted with inert gas, such as air or nitrogen. This process is widely known as a so-called thin film type sulfonation process and disclosed in, for example, U.S. Pat. Nos. 3,328,460, 3,427,342 and 3,839,391. This process has an advantage in that alkylbenzenes can be continuously sulfonated. However, there is a problem with regard to this process in that partially carbonized adherent deposits are adhered onto the surface of a reaction wall along which the starting alkylbenzenes are flowed downward. The formation or generation of the deposits onto the surface of a reaction wall causes irregularities in the flow of the stream of the thin film, whereby side reactions are accelerated. As a result, the properties of the sulfonated product are markedly impaired. for this reason, in the case were alkylbenzenes are commercially or industrially sulfonated according to the thin film type sulfonation process, there is a disadvantage in that the sulfonation reactor must be inevitably shut down and the surface of a reaction wall thereof cleaned at regular intervals.

It is considered that the formation of the above mentioned deposits on the surface of a reaction wall is caused by the presence of small or slight amounts of impurities contained in the starting alkylbenzenes. That is to say, the alkylbenzenes to be sulfonated are generally produced by the reaction of benzene and alkyl halides in the presence of a FriedelCrafts catalyst, such as, anhydrous aluminum chloride, or by the alkylation of benzene with olefins in the presence of sulfuric acid or a hydrogen fluoride catalyst. However, the alkylbenzenes obtained in these reactions unavoidably contain impurities, such as, catalyst residues, unreacted raw materials, byproducts and the like, although the produced alkylbenzenes are subjected to a purification process, such as rectification. These resultant impurities contained in small or slight amounts in the starting alkylbenzenes are considered to cause the formation of the deposits on the surface of a reaction wall.

In order to obviate the above mentioned problem in the thin film type sulfonation process of alkylbenzenes, it has been proposed, in U.S. Pat. No. 2,806,875, that alkylbenzenes be purified by a series of steps involving sulfuric acid extraction, alkali washing and rectification, in that order. However, based on the inventors' experience, the formation of the deposits onto the surface of a reaction wall cannot be fully prevented by such purification steps.

After intensive studies of the correlation between the impurities contained in the starting alkylbenzenes and the formation of the deposits on the surface of a reaction wall, the present inventors have found that the deposits on the surface of a reaction wall are poly-sulfonated products of olefins contained in the starting alkylbenzenes as impurities. That is to say, the starting alkylbenzenes are generally produced from olefins, or alkyl halides and benzene, as mentioned hereinabove, and the produced alkylbenzenes unavoidably contain at least approximately 100 ppm and up to approximately 2000 ppm of olefins as impurities. As a result, in the case where these alkylbenzenes are used as a starting material in the thin film type sulfonation process, the molar ratio of sulfur trioxide to the olefins becomes remarkably high, as compared with the molar ratio of sulfur trioxide to the alkylbenzenes. In addition, the rate of sulfonation of olefins is faster than that of alkylbenzens. Therefore, the olefin impurities in the alkylbenzenes are sulfonated consecutively in preference to the starting alkylbenzenes at the initial stage of the reaction. Thus, adherent poly-sulfonated products are formed via mono-sulfonated products and adhered onto the surface of a reaction wall.

Accordingly, the formation of the deposits onto the surface of a reaction wall can be prevented in the thin film type sulfonation process of alkylbenzenes when the olefin impurities contained in the starting alkylbenzenes are completely removed. However, the removal of the olefin impurities in an amount of less than 10 ppm from the alkylbenzenes is not practical from an economical point of view.

Various improvements in the sulfonation process in which sulfur trioxide gas is used are known. For instance, U.S. Pat. No. 3,864,375 discloses a process for thin film type sulfonation of olefins or fatty alcohols by the addition of a small amount of a non-ionic surface active agent, whereby the color deterioration of the sulfonated products can be improved and the deposition of the products on the surface of the reaction wall can be prevented. However, we have found that, in the case where alkylbenzenes are sulfonated, this process is not useful.

Furthermore, U.S. Pat. No. 4,113,765 discloses the addition of sulfuric acid or an alkyl benzene sulfonic acid to accelerate the sulfonation reaction in the case where alkylaromatics having a relatively high molecular weight and having a relatively low reactivity are sulfonated in an inert solvent. However, this process is not concerned with a thin-film type sulfonation process. In the case where this process is applied to the thin film type sulfonation of an alkyl benzene, it is expected that the formation of the adherent deposits on the surface of a reaction wall is increased due to the acceleration of the reaction. In fact, we have found that, in the case where an alkyl benzene is sulfonated in thin film type sulfonation by the addition of sulfuric acid, the formation of the undesired deposits on the surface of a reaction wall is increased.

Contrary to the above, we have found that, in the case where an alkyl benzene is sulfonated in thin film type sulfonation by the addition of an alkylbenzene sulfonic acid, no substantial amount of the adherent deposits is unexpectedly formed on the surface of a reaction wall.

SUMMARY OF THE INVENTION

Accordingly, an object of this invention is to obviate the above mentioned problem in the prior arts and to provide an improved thin film type sulfonation process of alkylbenzenes in which the above mentioned formation of deposits on the surface of a reaction wall is effectively prevented.

Other objects and advantages of this invention will be apparent from the following description.

In accordance with the present invention, there is provided an improved process for effecting the thin film sulfonation of alkylbenzenes containing small amounts of olefins as impurities, in which a feed stream of the alkylbenzenes is flowed downward in the form of a thin film along a surface of a reaction wall of a sulfonation reactor and is contacted with a gaseous stream of sulfur trioxide diluted with inert gas, wherein 2 through 20 parts by weight, based on 100 parts by weight of said alkylbenzenes, of at least one member selected from the group consisting of alkylbenzene sulfonic acids having alkyl groups of 1 through 20 carbon atoms and benzenesulfonic acid are added to the alkylbenzene prior to the contact thereof with the diluted gaseous sulfur trioxide.

DESCRIPTION OF THE PREFERRED EMBODIMENTS

The starting alkylbenzenes employed in the thin film type sulfonation process of this invention include those which are produced by any known processes. Examples of such alkylbenzenes are alkylbenzenes produced by a Friedel-Crafts reaction of benzene and alkyl halides or alkylbenzenes produced by the reaction of benzene and olefins in the presence of, for example, a hydrogen fluoride catalyst. Those synthetic alkylbenzenes are purified, before use, by any conventional purification method, including rectification. It should be noted that olefins as impurities, which cause the formation of the deposits on the surface of a reaction wall, cannot be completely removed from the alkylbenzene by conventional purification methods, such as, rectification. There is no critical chain length of the alkyl groups of the starting alkylbenzenes employed in this thin film type sulfonation process. For instance, in the case where alkylbenzene sulfonic acids suitable for use in the production of surface active agents are produced, alkylbenzenes having alkyl groups of 8 to 18, especially 10 to 14 carbon atoms can be preferably employed, as the starting material, in the thin film type sulfonation process of this invention.

As mentioned hereinabove, in accordance with this invention, the alkylbenzene sulfonic acids and/or benzenesulfonic acid are added to the starting alkylbenzenes, as a deposition preventing agent, in an amount of 2 through 20 parts by weight, preferably 5 through 20 parts by weight, based on 100 parts by weight of the starting alkylbenzenes, before the starting alkylbenzenes are contacted with diluted gaseous sulfur trioxide. In the case where the addition amount of the deposition preventing agent is less than 2 parts by weight based on 100 parts by weight of the starting alkylbenzenes, the formation of the deposits on the surface of a reaction wall cannot be effectively prevented. Contrary to this, when the addition amount of the deposition preventing agent is more than 20 parts by weight, based on 100 parts by weight of the starting alkylbenzenes, the formation of the deposits on the surface of a reaction wall are effectively prevented, but sulfonated products are colored. The addition of the deposition preventing agents can be effected in any manner, so long as they are added to the starting alkylbenzenes prior to the contact of the starting alkylbenzenes with the diluted gaseous sulfur trioxide in the reactor. For instance, the deposition preventing agents can be previously mixed with the starting alkylbenzenes or added to the starting alkylbenzenes just before the starting alkylbenzenes are fed to a sulfonation reactor.

The alkylbenzene sulfonic acids employed in the thin film type sulfonation process of this invention include those which have alkyl groups 1 through 20, preferably 1 through 18 carbon atoms. Examples of such alkylbenzene sulfonic acids are toluene sulfonic acid, ethyl benzene sulfonic acid, hexyl benzene sulfonic acid, octyl benzene sulfonic acid, tecyl benzene sulfonic acid, dodecyl benzene sulfonic acid, tetradecyl benzene sulfonic acid, hexadecyl benzene sulfonic acid and octadecyl sulfonic acid.

The thin film sulfonation of alkylbenzenes according to this invention can be effected in any conventional manner, except that the specified amount of alkylbenzene sulfonic acid and/or benzensulfonic acid must be previously added to the starting alkylbenzenes. The length of the flow of the thin film along the surface of a reaction wall is generally within the range of from 1 to 10 m. The sulfonation reaction conditions can be appropriately selected from any conventional conditions of the thin film type sulfonation process. For instance, the gaseous sulfur trioxide employed in the sulfonation reaction can be diluted with an inert gas, such as air and nitrogen, to a concentration of sulfur trioxide of 1 through 12% by volume, and fed to the reactor in such an amount that the molar ratio of sulfur trioxide to the alkylbenzenes is within the range of from 1.0 to 1.5. The sulfonation reaction can be carried out at a temperature of from 20° to 120° C., preferably from 40° to 80° C.

EXAMPLE

This invention now will be further illustrated by, but is by no means limited to, the following Examples.

EXAMPLE 1

To alkylbenzenes having a molecular weight of 243 and containing 250 ppm of olefins as impurities, alkylbenzene sulfonic acids having alkyl groups of 10 through 13 carbon atoms were added, and the mixture was sulfonated in a double column type thin film sulfonation reactor under the conditions mentioned below. The alkylbenzenes employed as the starting material were prepared by a FriedelCrafts reaction of benzene and alkyl chlorides.

| | |
|---|---|
| Feed rate of alkylbenzenes: | 300 kg/m hr |
| Molar ratio of SO$_3$ to alkylbenzenes: | 1.05 |
| Flow rate of diluted gaseous sulfur trioxide: | 4.5 Nm$^3$/min. |
| Temperature of cooling water in reactor: | 20° C. |
| Interval of reaction operating time: | 10 hr |

The correlations of (i) the addition amounts of the alkylbenzene sulfonic acids and (ii) the amount of the deposits onto the surface of a reaction wall and the properties of the sulfonated products obtained in the above experiments are shown in Table 1, below. In addition, a comparative experiment was conducted in a manner as described above, except that no alkylbenzene sulfonic acid was added to the starting alkylbenzenes.

TABLE 1

| Run No. | 1*[1] | 2 | 3 | 4 | 5 | 6 | 7*[1] |
|---|---|---|---|---|---|---|---|
| Addition amount of alkylbenzene sulfonic acids*[2] (parts by weight) | 1 | 2 | 5 | 10 | 20 | 40 | 0 |
| Amount of deposits onto surface of a reaction wall (mg)*[3] | 10 | 0 | 0 | 0 | 0 | 0 | 1500 |
| Properties of products | | | | | | | |
| (a) Unreacted oil content *[4] (% by weight) | 1.2 | 1.2 | 1.25 | 1.3 | 1.2 | 1.3 | 1.3 |
| (b) Color*[5] | 0.009 | 0.008 | 0.007 | 0.007 | 0.008 | 0.010 | 0.010 |

*[1]Comparative Example
*[2]Parts by weight based on 100 parts by weight of the starting alkylbenzenes
*[3]After 10 hrs reaction operation, the deposits on the surface of a reaction wall were scraped and weight.
*[4]Content of oils extracted with petroleum ether, based on active matter.
*[5]Absorbance in 420 m of 5% aqueous solution of the products as measured in a 10 mm cell.

EXAMPLE 2

The sulfonation reactions were carried out in a manner as described in Example 1, except that various additives listed in Table 2 below were used.

The results are shown in Table 2 below. As is clear from the results shown in Table 2 below, although the content of the unreacted oil in the product is substantially similar in each run, the undesired formation of the deposit on the surface of the reaction wall was observed in Run Nos. 2, 3, 4 and 5, but not in Run No. 1 of the present invention.

TABLE 2

| Run No. | 1 | 2* | 3* | 4* | 5* |
|---|---|---|---|---|---|
| Species of additives | alkylbenzene sulfonic Acid (C10-14) | Concentrated sulfuric acid (98%) | oleum (20%) | Lauryl Alcohol with 3 sole ethylene oxide | — |
| addition amount of additives (parts by weight) | 2 | 2 | 2 | 2 | 0 |
| amount of deposit onto surface of reaction wall (mg) | 0 | 2,200 | 2,500 | 1,100 | 1,500 |
| properties of product | | | | | |
| (a) unreacted oil (% by weight) | 1.30 | 1.25 | 1.20 | 1.30 | 1.30 |
| (b) Color | 0.007 | 0.013 | 0.017 | 0.022 | 0.010 |

*Comparative Example

EXAMPLE 3

The sulfonation reactions were carried out in a manner as described in Example 1, except that alkylbenzenes having a molecular weight of 243 and containing 300 ppm of olefins as impurities were used as the starting alkylbenzenes and p-toluene sulfonic acid was used as the deposition preventing agent. The alkylbenzenes used in this Example were prepared by alkylation reaction of benzene with olefins in a conventional manner. The results are shown in Table 3, below.

TABLE 3

| Run No. | 1* | 2 | 3 | 4* |
|---|---|---|---|---|
| Addition amount of p-toluene sulfonic acid (parts by weight) | 1 | 2 | 5 | 0 |
| Amount of deposits on surface of a reaction wall (mg) | Trace | 0 | 0 | 2000 |

TABLE 3-continued

| Run No. | 1* | 2 | 3 | 4* |
|---|---|---|---|---|
| Properties of products | | | | |
| (a) Unreacted oil content (% by weight) | 1.2 | 1.2 | 1.15 | 1.25 |
| (b) Color | 0.009 | 0.008 | 0.008 | 0.012 |

*Comparative Example

EXAMPLE 4

The sulfonation reactions were carried out in a manner as described in Example 1, except that alkylbenzenes having alkyl groups of 10 to 14 carbon atoms and containing 1200 ppm of olefins as impurities were used as the starting alkylbenzenes, and alkylbenzene sulfonic acids having alkyl groups of 8 to 10 carbon atoms were used as the deposition preventing agent. The alkylbenzenes used in this Example were prepared by the alkylation of benzene with olefins, which were obtained from the dehydrochlorination of chlorinated paraffins.

The results are shown in Table 4, below.

TABLE 4

| Run No. | 1* | 2 | 3 | 4 | 5 | 6 | 7* |
|---|---|---|---|---|---|---|---|
| Addition amount of alkylbenzene sulfonic acids (parts by weight) | 1 | 2 | 5 | 10 | 20 | 40 | 0 |
| Amount of deposits onto surface of a reaction wall (mg) | 5 | 0 | 0 | 0 | 0 | 0 | 3500 |
| Properties of products | | | | | | | |
| (a) Unreacted oil content (% by weight) | 1.2 | 1.2 | 1.3 | 1.3 | 1.2 | 1.3 | 1.3 |
| (b) Color | 0.019 | 0.017 | 0.016 | 0.015 | 0.016 | 0.016 | 0.022 |

*Comparative Example

As is clear from the results shown in Tables 1 through 4, the formation of the deposits on the surface of a reaction wall can be effectively prevented by the thin film type sulfonation process according to this invention. Furthermore, according to this invention, the color of the sulfonated products can be improved, as compared with the conventional process.

We claim:

1. In a process for effecting the thin film sulfonation of alkylbenzene containing small amounts of olefins as impurities, in which a feed stream of the alkylbenzene is flowed downward in the form of a thin film along a surface of a reaction wall of a sulfonation reactor and is contacted with a gaseous stream of sulfur trioxide diluted with inert gas, the improvement wherein:

2 through 20 parts by weight, based on 100 parts by weight of said alkylbenzene, of at least one member selected from the group consisting of alkylbenzene sulfonic acids having alkyl groups of 1 through 20 carbon atoms and benzenesulfonic acid are added to the alkylbenzene prior to the contact thereof with the diluted gaseous sulfur trioxide, whereby the presence of said at least one of said alkylbenzene sulfonic acids and said benzene sulfonic acid substantially prevents the formation of deposits on the surface of the reaction wall.

2. A process as claimed in claim 1, wherein said alkylbenzene sulfonic acids are selected from the group consisting of alkylbenzene sulfonic acids having alkyl groups of 1 through 8 carbon atoms.

3. A process as claimed in claim 1, wherein said alkylbenzene sulfonic acids are toluene sulfonic acid, ethyl benzene sulfonic acid, hexyl benzene sulfonic acid, octyl benzene sulfonic acid, decyl benzene sulfonic acid, dodecyl benzene sulfonic acid, tetradecyl benzene sulfonic acid, hexadecyl benzene sulfonic acid and octadecyl sulfonic acid.

4. A process as claimed in claim 1, wherein said alkylbenzene is at least one member selected from alkylbenzenes having alkyl groups of 8 to 18 carbon atoms.

5. A process as claimed in claim 1, wherein said alkylbenzene is at least one member selected from alkylbenzenes having alkyl groups of 10 to 14 carbon atoms.

6. A process as claimed in claim 1, wherein the at least one member selected from the group consisting of alkylbenzene sulfonic acid having alkyl groups of 1 through 20 carbon atoms and benzene sulfonic acid is used in an amount of 5 through 20 parts by weight, based on 100 parts of said alkylbenzene.

* * * * *